("12") United States Patent
Cai et al.

(10) Patent No.: US 10,499,916 B2
(45) Date of Patent: Dec. 10, 2019

(54) SURGICAL STAPLING LOADING UNIT

(71) Applicant: Covidien LP, Mansfield, MA (US)

(72) Inventors: Longsheng Cai, Shanghai (CN);
Xiliang Zhang, Shanghai (CN);
Zhaokai Wang, Shanghai (CN)

(73) Assignee: Covidien LP, Mansfield, MA (US)

( * ) Notice: Subject to any disclaimer, the term of this patent is extended or adjusted under 35 U.S.C. 154(b) by 285 days.

(21) Appl. No.: 15/531,783

(22) PCT Filed: Dec. 11, 2014

(86) PCT No.: PCT/CN2014/093563
§ 371 (c)(1),
(2) Date: May 31, 2017

(87) PCT Pub. No.: WO2016/090594
PCT Pub. Date: Jun. 16, 2016

(65) Prior Publication Data
US 2017/0340326 A1 Nov. 30, 2017

(51) Int. Cl.
*A61B 17/072* (2006.01)
*A61B 17/00* (2006.01)
(Continued)

(52) U.S. Cl.
CPC .. *A61B 17/07207* (2013.01); *A61B 17/00234* (2013.01); *A61B 17/064* (2013.01);
(Continued)

(58) Field of Classification Search
CPC ................ A61B 17/068; A61B 17/072; A61B 17/07207; A61B 17/115; A61B 17/1155;
(Continued)

(56) References Cited

U.S. PATENT DOCUMENTS 3,193,165 A   7/1965   Akhalaya et al.
3,388,847 A   6/1968   Kasulin et al.
(Continued)

FOREIGN PATENT DOCUMENTS

CA      908529 A    8/1972
CA     2805365 A1   8/2013
(Continued)

OTHER PUBLICATIONS

Japanese Office Action dated Jul. 17, 2018 in JP Appln. No. 2017530597.
(Continued)

*Primary Examiner* — Scott A Smith

(57) ABSTRACT

A surgical loading unit (10) for use with a surgical handle assembly (1000) includes a handle mount (12) dimensioned for mounting to the handle assembly (1000), an outer member (56) extending from the handle mount (12), a staple cartridge assembly (16) mounted to the distal end of the outer member (56), and an anvil assembly (18) couplable relative to the staple cartridge assembly (16). A staple pusher (60) is at least partially disposed within the outer member (56) and operatively coupled to the staple cartridge assembly (16). The staple pusher (60) is adapted for longitudinal movement to eject staples from the staple cartridge assembly (16). An anvil approximator (94) is at least partially disposed within the outer member (56) and is operatively coupled to the anvil assembly (18). The anvil approximator (94) is adapted for movement between first and second positions corresponding to closed and open conditions of the anvil assembly (18) relative to the staple cartridge assembly (16). A lock member (24) is mounted to the handle mount (12). The lock member (12) is adapted to move from a lock position in secured engagement with the staple pusher (60) and the anvil approximator (94) to a release position releasing the staple pusher (60) and the anvil approximator (94)
(Continued)

upon mounting of the handle mount (12) relative to the surgical handle assembly (1000).

17 Claims, 15 Drawing Sheets

(51) Int. Cl.
*A61B 17/115* (2006.01)
*A61B 17/064* (2006.01)
*A61B 17/068* (2006.01)

(52) U.S. Cl.
CPC ......... *A61B 17/1155* (2013.01); *A61B 17/068* (2013.01); *A61B 17/072* (2013.01); *A61B 2017/0046* (2013.01); *A61B 2017/00477* (2013.01); *A61B 2017/0725* (2013.01); *A61B 2017/07257* (2013.01); *A61B 2017/07271* (2013.01)

(58) Field of Classification Search
CPC .. A61B 2017/07214; A61B 2017/2923; A61B 2017/2927; A61B 2017/2929; A61B 2017/00473; A61B 2017/07278; A61B 2017/07257; A61B 2017/07271
USPC .............. 227/19, 175.2, 175.3, 176.1, 180.1; 606/139, 153, 213, 219
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |

(56) References Cited

U.S. PATENT DOCUMENTS

| | | |
|---|---|---|
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |

(56) References Cited

U.S. PATENT DOCUMENTS

| | | |
|---|---|---|
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,939,343 B2 * | 1/2015 | Milliman .......... A61B 17/07207 227/176.1 |
| 9,566,064 B2 * | 2/2017 | Williams ............. A61B 17/068 |
| 9,757,126 B2 * | 9/2017 | Cappola .............. A61B 17/072 |
| 9,918,717 B2 * | 3/2018 | Czernik ........... A61B 17/07207 |
| 10,045,782 B2 * | 8/2018 | Murthy Aravalli .. A61B 17/068 |
| 10,085,750 B2 * | 10/2018 | Zergiebel ......... A61B 17/07207 |
| 10,285,698 B2 * | 5/2019 | Cappola .............. A61B 17/105 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |

(56) References Cited

U.S. PATENT DOCUMENTS

| | | |
|---|---|---|
| 2009/0099566 A1 | 4/2009 | Maness et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0301097 A1* | 12/2010 | Scirica ............ A61B 17/07207 227/176.1 |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0305627 A1 | 12/2012 | Milliman et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2017/0027575 A1* | 2/2017 | Murthy Aravalli .. A61B 17/068 |

FOREIGN PATENT DOCUMENTS

| | | |
|---|---|---|
| CN | 101843509 A | 9/2010 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1709911 A1 | 10/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2006289064 A | 10/2006 |
| JP | 2007516730 A | 6/2007 |
| JP | 2009045452 A | 3/2009 |
| JP | 2011115594 A | 6/2011 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | WO03030743 A2 | 4/2003 |
| WO | 2008/107918 A1 | 9/2008 |

OTHER PUBLICATIONS

International Search Report for PCT/CN14/093563 date of completion is Aug. 31, 2015 (4 pages).

Chinese Office Action dated Jun. 28, 2019, received Jul. 25, 2019, issued in CN Appln. No. 201480083971.

* cited by examiner

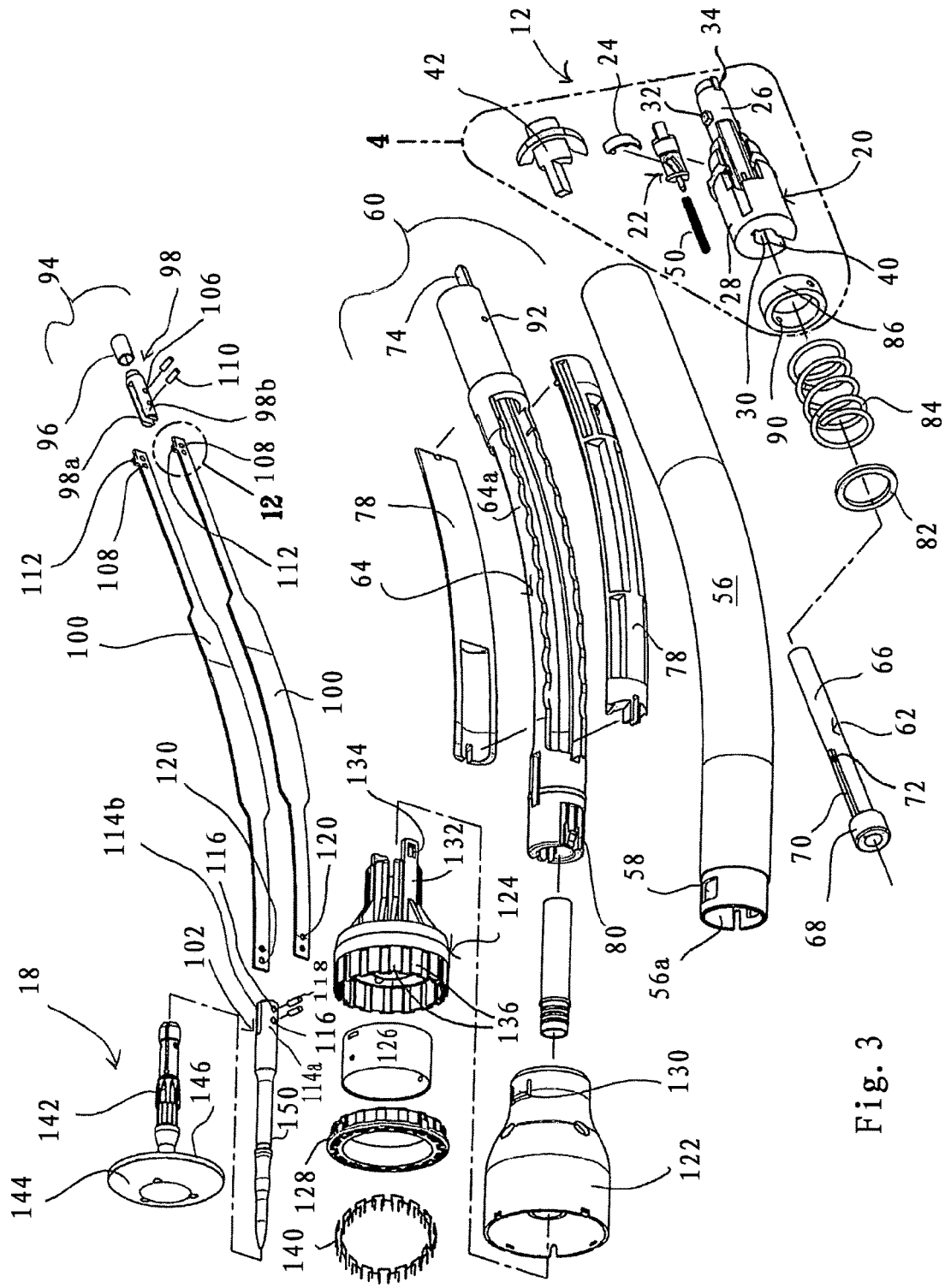

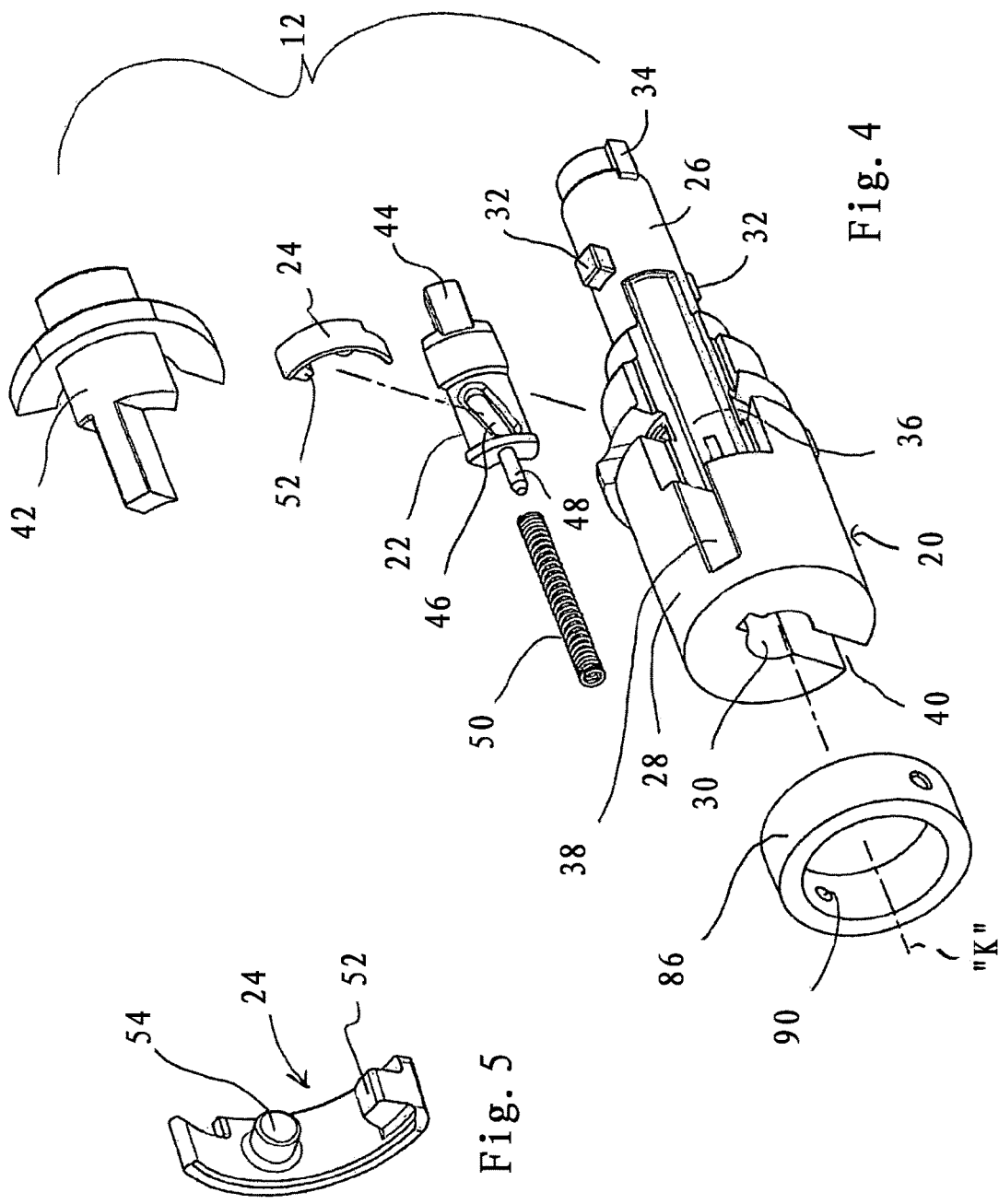

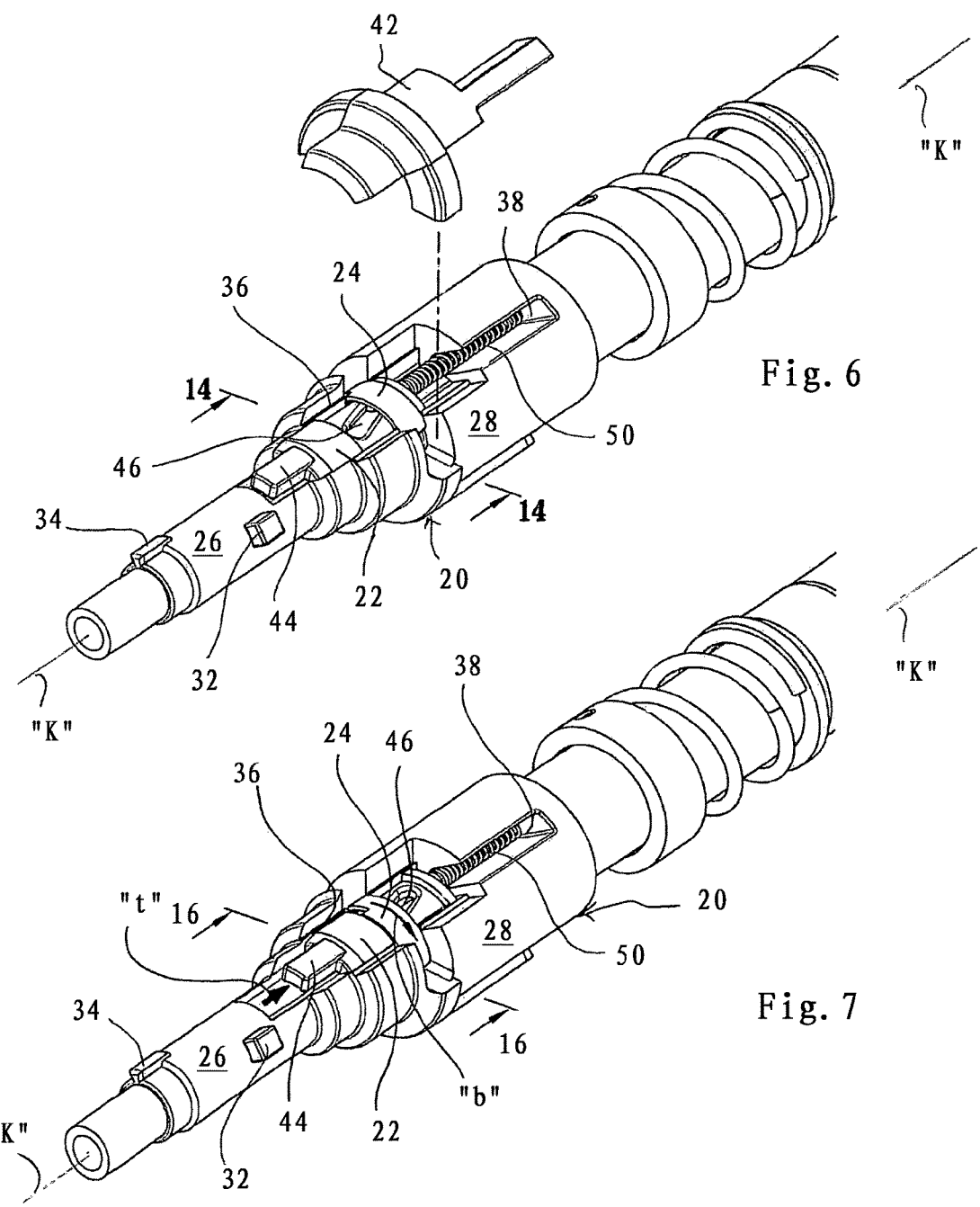

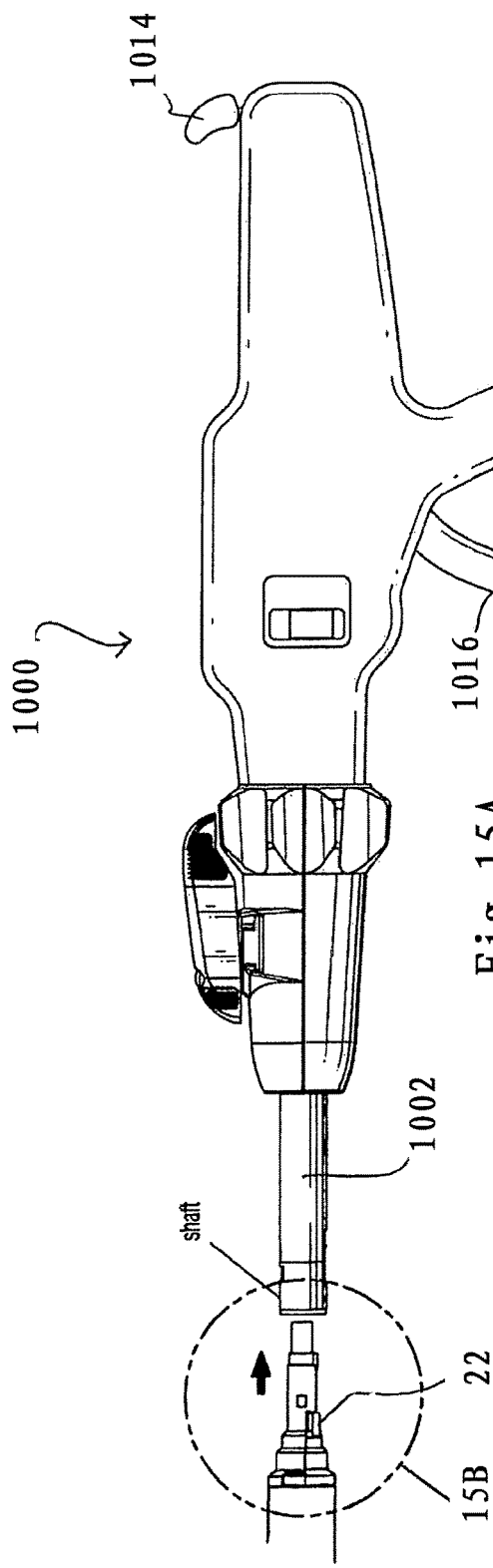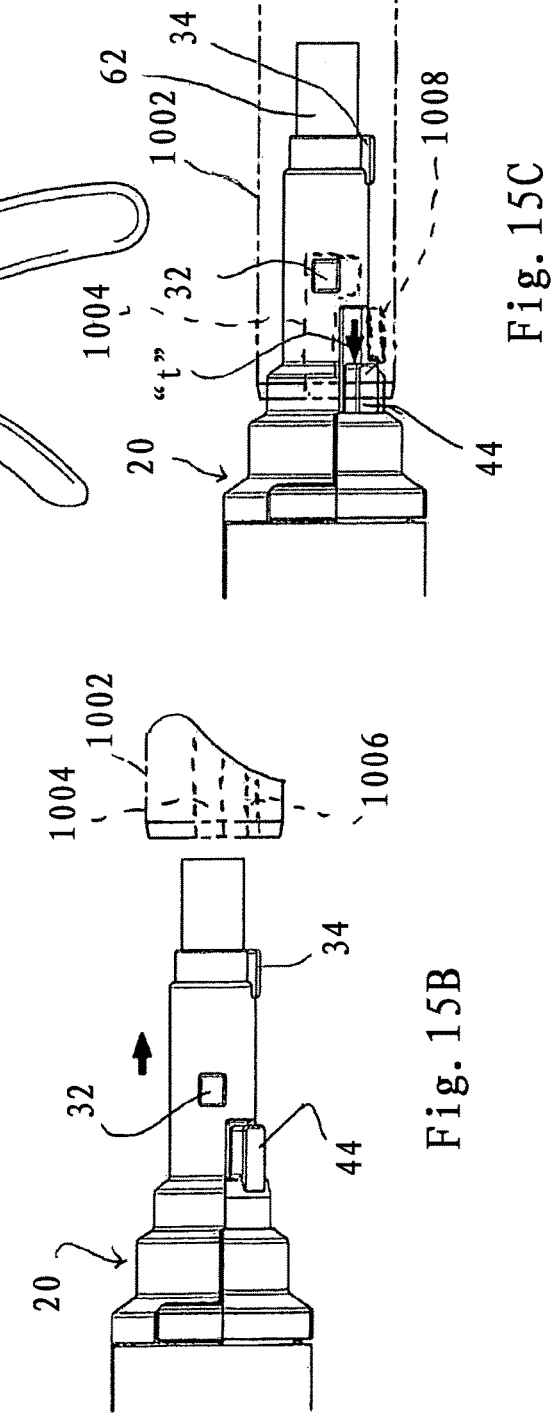
Fig. 15A
Fig. 15B
Fig. 15C

SURGICAL STAPLING LOADING UNIT

CROSS-REFERENCE TO RELATED APPLICATIONS

This application is a National Stage Application of PCT/CN14/093563 under 35USC § 371 (a), the disclosures of the above-identified application is hereby incorporated by reference in its entirety.

BACKGROUND

1. Technical Field

The present disclosure relates to a surgical stapling loading unit for use with a surgical handle assembly. More particularly, the present disclosure relates to a stapling loading unit for use with a surgical handle assembly and having a lockout mechanism for retaining a staple pusher and an anvil approximator of the loading unit in their respective pre-fired positions until the loading unit is properly attached to the surgical handle assembly.

2. Background of Related Art

Surgical staplers for applying staples to tissue are well known. Such staplers include single use devices which are preloaded with one or more staples and are disposable after a single use. Multiple use devices are also available and are preloaded with a plurality of staples. These multiple use devices are disposable after the supply of staples has been exhausted or a surgical procedure has been completed. If the supply of staples is exhausted prior to completion of a surgical procedure, a new surgical stapler may be required to complete the surgical procedure. The use of additional surgical staplers for a single surgical procedure can be expensive.

In order to address the high expense of using multiple surgical staplers for a single procedure, surgical staplers with replaceable staple cartridges have been developed. In such surgical staplers, staples are housed within a cartridge. When the staples in the cartridge have been exhausted, the cartridge can be removed and replaced with a new cartridge having an additional supply of staples.

Covidien, LP, has manufactured and marketed stapling systems having replaceable cartridges, such as the Multifire ENDO GIA™ 30 and Multifire ENDO GIA™ 60 systems, for a number of years. These systems include a surgical stapling handle assembly and a surgical loading unit. The loading unit may be a single use loading unit (SULU) or a multiple use loading unit (MULU). The loading unit includes a body and an end effector, and is attached to the handle assembly immediately prior to surgery. The end effector may include a cartridge which houses a plurality of staples. After use, the loading unit can be removed relative to the handle assembly and replaced with a new loading unit to perform additional stapling and/or cutting operations. A drive assembly is supported within the loading unit and is engagable with a control rod of the surgical handle assembly to control operation of the loading unit.

Although, these systems have provided significant clinical benefits, improvements are still possible. Accordingly, it would be desirable to provide an improved stapling loading unit for use in a surgical stapling system adapted to perform, e.g., a circular or end-to-end anastomosis, and which retains or locks the staple pusher assembly and/or the anvil approximator assembly in a pre-fired position until the loading unit is attached to the surgical handle assembly of the system.

SUMMARY

Accordingly, a surgical loading unit for use with a surgical handle assembly includes a handle mount dimensioned for mounting to the handle assembly, an outer member extending from the handle mount and having proximal and distal ends, a staple cartridge assembly mounted to the distal end of the outer member and having a plurality staples, and an anvil assembly couplable relative to the staple cartridge assembly. A staple pusher is at least partially disposed within the outer member and is operatively coupled to the staple cartridge assembly. The staple pusher is adapted for longitudinal movement to eject the staples. An anvil approximator is at least partially disposed within the outer member and is operatively coupled to the anvil assembly. The anvil approximator is adapted for movement between first and second positions corresponding to closed and open conditions of the anvil assembly relative to the staple cartridge assembly. The loading unit further includes a lock member which is mounted to the handle mount. The lock member is adapted to move from a lock position in secured engagement with the staple pusher and the anvil approximator to a release position releasing the staple pusher and the anvil approximator upon mounting of the handle mount relative to the surgical handle assembly.

In embodiments, the lock member is adapted for rotational movement about the longitudinal axis to move from the lock position to the release position. In certain embodiments, a guide member having a guide channel arranged at an angle relative to the longitudinal axis is provided. The lock member may be at least partially received within the guide channel of the guide member and is adapted to traverse the channel during movement of the lock member from the lock position to the release position. In some embodiments, the lock member includes a lock tab and a channel tab. The lock tab is operatively engagable with the staple pusher and the anvil approximator when the lock member is in the lock position. The channel tab is received within the guide channel of the guide member and is adapted to traverse the channel.

In other embodiments, the guide member is adapted to move relative to the handle mount between a retracted position corresponding to the lock position of the lock member and an advanced position corresponding to the release position of the lock member. The guide member may be normally biased toward the retracted position. A spring may be operatively engagable with the handle mount and the guide member, and dimensioned to normally bias the guide member to the retracted position. In some embodiments, the guide member is dimensioned to engage the handle assembly during mounting of the handle mount relative to the handle assembly causing movement of the guide member to the advanced position thereof.

In certain embodiments, the staple pusher includes a staple connector which is at least partially disposed within the handle mount, and incorporates a staple lock surface. The staple lock surface is engaged by the lock member when in the lock position of the lock member and released from the lock member when in the release position of the lock member. The staple pusher may be normally biased toward a proximal position thereof.

In other embodiments, the anvil approximator includes an anvil band which is at least partially disposed within the handle mount. The anvil band has an anvil lock surface which is engaged by the lock member when in the lock position of the lock member and released from the lock member when in the release position of the lock member.

In embodiments, the staple cartridge includes an annular array of staples and the anvil assembly includes an annular anvil head cooperable with the annular array of staples to perform a circular or an end-to-end anastomosis.

In another aspect of the present disclosure, a surgical system for performing a circular or an end-to-end anastomosis includes a handle assembly and a loading unit mountable to the handle assembly. The handle assembly includes a frame, a staple actuator and an anvil actuator each being at least partially disposed within the frame, and at least one manual member for actuating at least one of the staple actuator and the anvil actuator. The loading unit includes a handle mount dimensioned for mounting to the frame of the handle assembly, an outer member extending from the handle mount and having proximal and distal ends, a staple cartridge assembly mounted to the distal end of the outer member, and an anvil assembly couplable relative to the staple cartridge assembly. The staple cartridge assembly includes a plurality staples arranged in an annular array. The anvil assembly includes an anvil shaft and an anvil head. A staple pusher is at least partially disposed within the outer member and operatively coupled to the staple cartridge assembly. The staple pusher is adapted for longitudinal movement to eject the staples to be crimped by the anvil head. The staple pusher is couplable to the staple actuator of the handle assembly upon mounting of the handle mount to the frame whereby movement of the at least one manual member causes corresponding movement of the staple pusher. An anvil approximator is at least partially disposed within the outer member and operatively coupled to the anvil assembly. The anvil approximator is adapted for movement between first and second positions corresponding to closed and open conditions of the anvil assembly relative to the staple cartridge assembly. The anvil approximator is couplable to the anvil actuator of the handle assembly upon mounting of the handle mount to the frame whereby movement of the at least one manual member causes corresponding movement of the anvil approximator between the first and second positions. The loading unit further includes a lockout mechanism which is mounted to the handle mount. The lockout mechanism includes a lock member and a guide member. The guide member is engagable with the frame of the handle assembly upon mounting of the handle mount to the frame to cause the lock member to rotate about the longitudinal axis from a lock position where the lock member is in secured engagement with the staple pusher and the anvil approximator, to a release position where the lock member releases the staple pusher and the anvil approximator.

In some embodiments, the guide member is adapted to move relative to the handle mount between a retracted position corresponding to the lock position of the lock member and an advanced position corresponding to the release position of the lock member. In certain embodiments, the lock member includes a channel tab and a locking tab. The locking tab is engagable with the staple pusher and with the anvil approximator when in the lock position of the lock member. The channel tab may be received within a guide channel defined within the guide member, and traverses the guide channel upon movement of the guide member between the retracted position and the advanced position. In some embodiments, the guide member is normally biased toward the retracted position thereof and the staple pusher is normally biased toward a proximal position thereof.

BRIEF DESCRIPTION OF THE DRAWINGS

Embodiments of the present disclosure will be readily appreciated by reference to the drawings wherein:

FIG. 3 is an exploded perspective view of the surgical loading unit;

FIG. 4 is an isolated view of the area of detail identified in FIG. 3 illustrating components of the handle mount of the surgical loading unit;

FIG. 5 is a perspective view of the lock member of the handle mount;

FIG. 6 is a perspective view with portions removed of the handle mount of the surgical loading unit illustrating the lock member in a lock position;

FIG. 7 is a perspective view of the handle mount illustrating the lock member in a release position;

FIG. 11 is an isolated view of the area of detail identified in FIG. 8;

FIG. 15A is a side plan view illustrating mounting of the handle mount of the loading unit to the handle assembly;

FIG. 15B is an enlarged isolated view of the area of detail identified in FIG. 15A;

FIG. 15C is a view illustrating the handle mount mounted to the handle assembly and the guide member in the advanced position corresponding to the release position of the lock member;

DETAILED DESCRIPTION OF THE EMBODIMENT(S)

Figure 1:
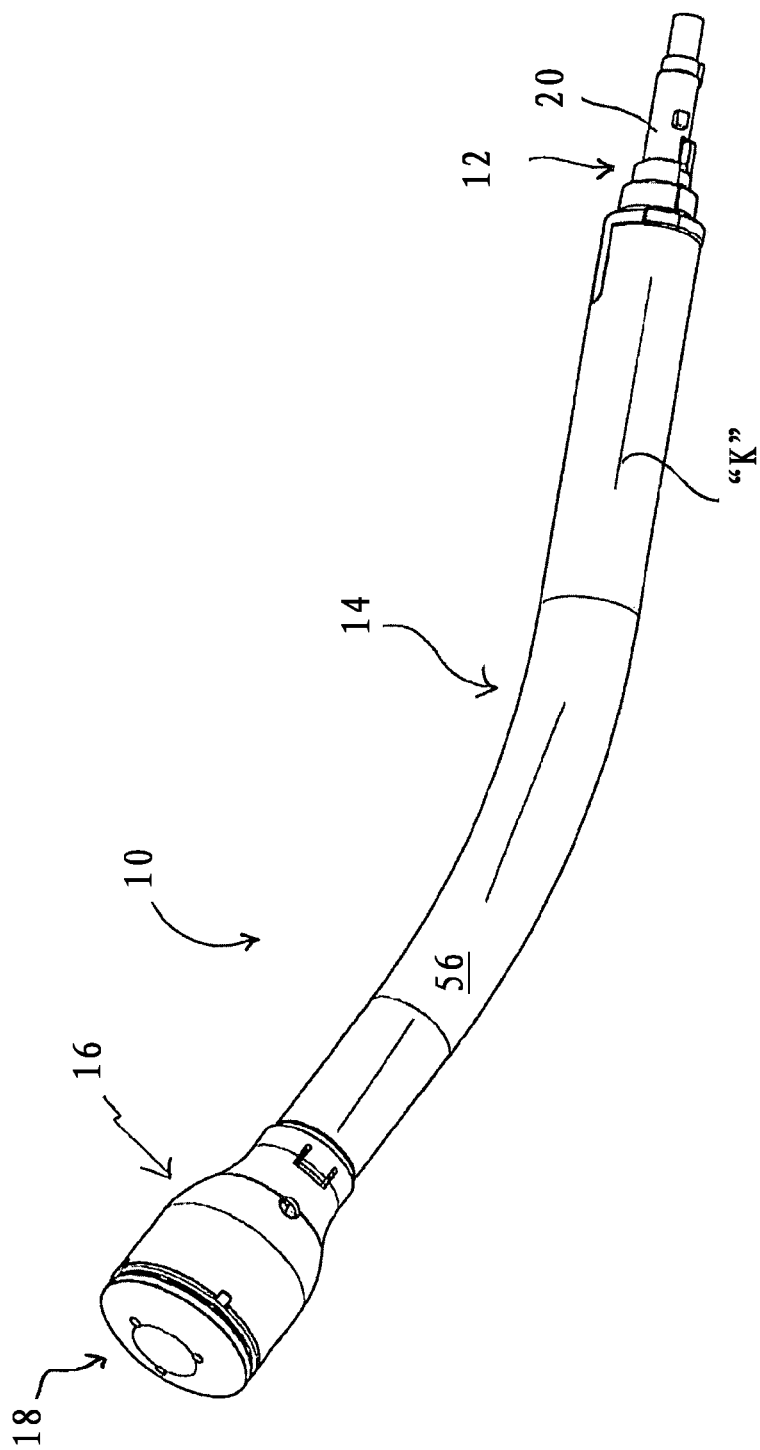
FIG. 1 is a perspective view of a surgical loading unit for performing a surgical stapling procedure in accordance with the principles of the present disclosure.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure. Like reference numerals may refer to similar or identical elements throughout the description of the figures.

Figure 2:
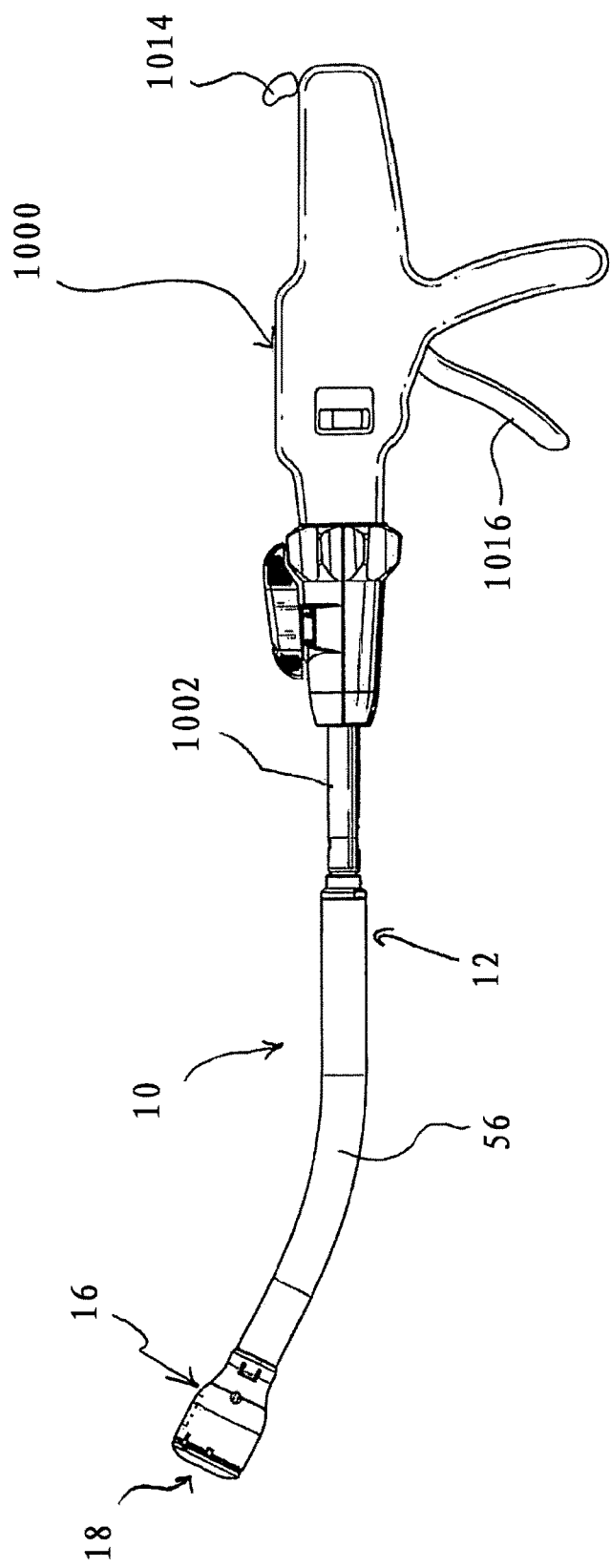
FIG. 2 is a side plan view of the surgical loading unit mounted to a surgical handle assembly.

Referring now to the drawings where like reference numerals indicate similar components throughout the several views, FIGS. 1-2 illustrate the surgical loading unit in accordance with the principles of the present disclosure. In FIG. 1, the surgical loading unit 10 is depicted in isolation while in FIG. 2 the surgical loading unit 10 is depicted connected to a surgical handle assembly 1000. The surgical loading unit 10 and the surgical handle assembly 1000 form a surgical system adapted to perform a surgical procedure on tissue e.g., a circular or end-to-end anastomosis on tubular organs. The loading unit 10 may be a single use loading unit (SULU). It is also contemplated that the loading unit 10 may be a multi-use loading unit (MULU) adapted, e.g., for sequential firing of one or more staples.

The surgical handle assembly 1000 may be any handle assembly having at least one actuator, and in some embodiments, two actuators adapted to control operation of the loading unit 10. It is contemplated that the surgical handle assembly 1000 may be reusable, i.e., it can be reused with a plurality of loading units 10, and may be used with loading units having different stapling functions such as, e.g., linear stapling of tissue. Further details of the handle assembly 1000 and its interaction with the surgical loading unit 10 will be discussed in greater detail hereinbelow.

Referring now to FIGS. 3-6, in conjunction with FIG. 1, the surgical loading unit 10 will be discussed. The surgical loading unit 10 includes a handle mount 12 and an elongated segment 14 extending from the handle mount 12 and defining a longitudinal axis "k". A staple cartridge assembly 16 and an anvil assembly 18 are each mounted relative to the elongated segment 14. The handle mount 12 includes a mount frame 20, a release or guide member 22 mounted to the mount frame 20 and a lock member 24 mounted relative to the guide member 22. The mount frame 20 defines a proximal mounting segment 26 of generally cylindrical configuration and a distal segment 28 also of general cylindrical configuration and defining a larger diameter than the proximal mounting segment 26. The mount frame 20 defines a longitudinal passage 30 extending completely through the proximal mounting segment 26 and the distal segment 28. The proximal mounting segment 26 has diametrically opposed outer tabs 32 and an alignment tab 34 disposed at the proximal end of the mount frame 20. The opposed tabs 32 and the alignment tab 34 may cooperate with corresponding structure in the handle assembly 1000 to properly orient and secure the loading unit 10 relative to the handle assembly 1000, e.g., in a bayonet coupling relation. The mount frame 20 further includes a channeled groove 36 which receives the guide member 22. The channeled groove 36 terminates in a distal spring slot 38 defined within the distal segment 28 of the mount frame 20. The mount frame 20 also defines a keyed slot 40 extending through its distal face. A mount cover 42 is releasably couplable to the mount frame 20, and may be removed to permit assembly of the various components of the handle mount 12.

With reference to FIGS. 3-7, the guide member 22 is adapted for reciprocal longitudinal movement relative to the mount frame 20 and within the channeled groove 36 between a retracted position (FIG. 6) corresponding to a lock position of the lock member 24 and an advanced position (FIG. 7) corresponding to a release position of the lock member 24. The guide member 22 includes a proximal guide tab 44, a cam slot 46 obliquely arranged with respect to the longitudinal axis "k" of the elongated segment 14 (FIG. 1) and a spring pin 48 extending from the distal end of the guide member 22. The proximal guide tab 44 engages corresponding structure within the handle assembly 1000 to move the guide member 22 in the direction of directional arrow "t" (FIG. 7) from the retracted position to the advanced position during linear insertion of the handle mount 12 within the handle assembly 1000. A coil spring 50 is at least partially mounted about the spring pin 48 and is disposed within the distal spring slot 38 of the mount frame 20. The coil spring 50 biases the guide member 22 toward the retracted position depicted in FIG. 6 thereby maintaining the lock member 24 in the lock position.

The lock member 24 is adapted for rotational movement about the longitudinal axis from the lock position (FIG. 6) to the release position (FIG. 7) to releasably secure the operating components in the elongated segment 14, i.e., the staple pusher and the anvil approximator, which respectively controls operation of the staple cartridge assembly 16 and the anvil assembly 18. As best depicted in FIGS. 4 and 5, the lock member 24 includes a lock tab 52 and a channel boss 54. The lock tab 52 is operatively engagable with the operating components of the elongated segment 14 when the lock member 24 is in the lock position, e.g., prior to mounting the handle mount 12 to the handle assembly 1000, and releases the operating components when in the release position, e.g., when the handle mount 12 is mounted within the handle assembly 1000. The channel boss 54 is at least partially received within the cam slot 46 of the guide member 22. Upon movement of the guide member 22 from the retracted position (FIG. 6) to the advanced position (FIG. 7), the channel boss 54 traverses the cam slot 46 of the guide member 22, which causes the lock member 24 to rotate through a predetermined arc of rotation relative to the longitudinal axis "k" in the direction of directional arrow "b" (FIG. 7) from its lock position to its release position. Further details of the operation of the lock member 24 will be discussed in greater detail hereinbelow.

With reference to FIGS. 8-11, in conjunction with FIG. 3, the elongated segment 14 includes an outer member 56, which in one embodiment, is in the form of an outer tube defining a longitudinal opening 56a (FIG. 3), and is mounted to the handle mount 12 through conventional arrangements. For example, the proximal end of the outer member 56 may be mounted about the distal segment 28 of the handle mount 12 and secured via the use of adhesives, cements, fasteners, etc. The distal end of the outer member 56 may include a reduced diameter with opposed rectangular shaped windows 58 (FIG. 3) to assist in mounting the staple cartridge assembly 16 to the outer member 56.

Disposed within the outer member 56 is a staple pusher 60 including a staple connector 62 and a staple pusher tube 64 extending from the staple connector 62. The staple connector 62 is at least partially disposed within the longitudinal passage 30 of the handle mount 12 and incorporates a proximal cylindrical segment 66 and a distal collar segment 68. The proximal cylindrical segment 66 of the staple connector 62 includes a raised spline 70 (FIGS. 3 and 10) which defines a staple lock surface in the form of a lock slot 72 through which the lock tab 52 of the lock member 24 extends when in the lock position of the lock member 24. During movement of the lock member 24 to the release position, the lock tab 52 traverses the lock slot 72 to be released from the spline 70 and permit distal longitudinal movement of the staple connector 62 and the staple pusher tube 64.

Figure 9:
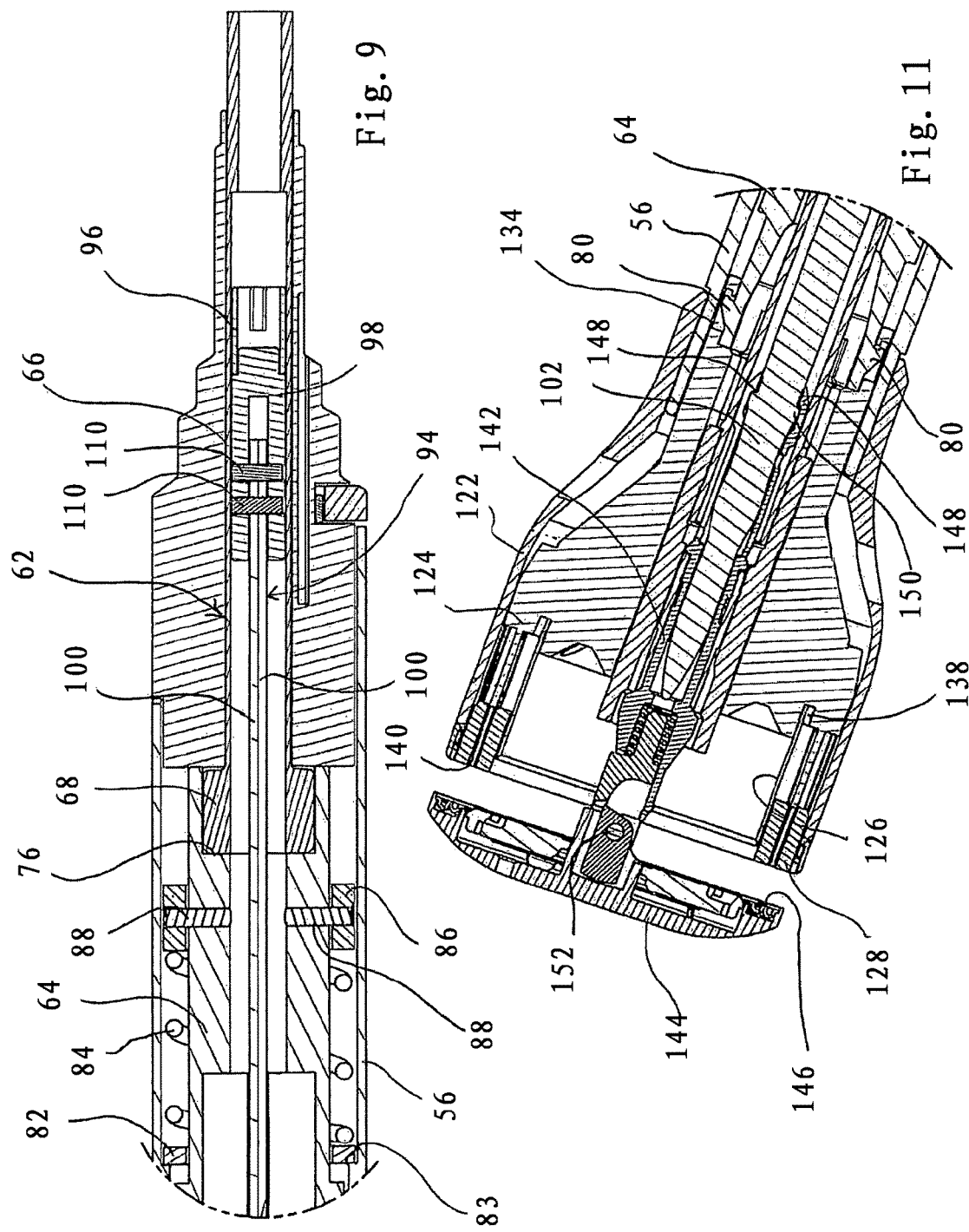
FIG. 9 is an isolated view of the area of detail identified in FIG. 8 illustrating a first side cross-sectional view of the handle mount with the lock member in the lock position.
Figure 10:
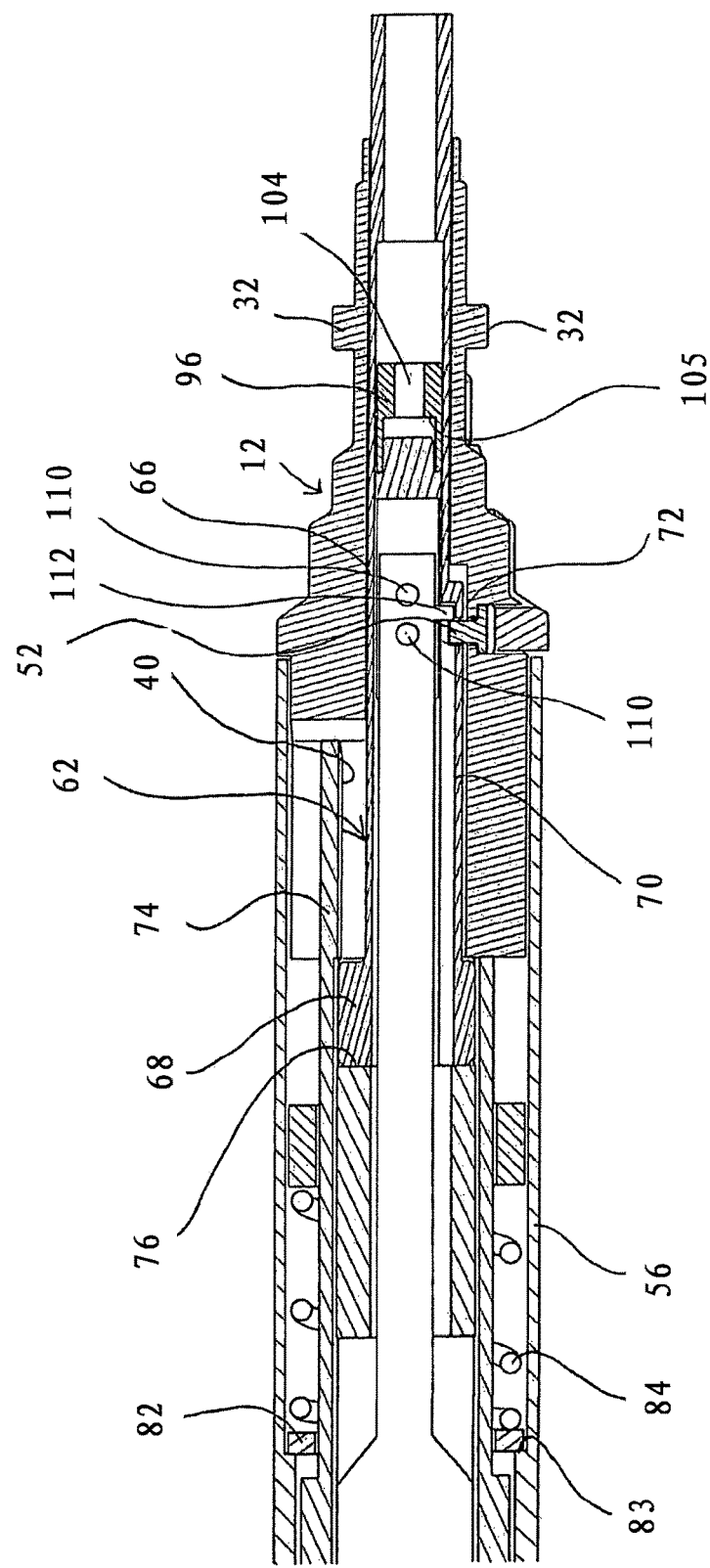
FIG. 10 is a second side cross-sectional view of the handle mount with the lock member in the lock position.

As best depicted in FIGS. 9-10, the staple pusher tube 64 includes an alignment rod 74 which is received within the keyed slot 40 of the handle mount 12 to properly orient the staple pusher tube 64 relative to the handle mount 12. (see also FIG. 3) The proximal end of the staple pusher tube 64 defines a recess 76 which accommodates the distal collar segment 68 of the staple connector 62 to connect the two components. Adhesives and or cements may be used to securely fix the staple connector 62 and the staple pusher tube 64. The staple pusher tube 64 may include opposed wall segments or spacers 78 which couple to the main body 64a of the staple pusher tube 64 (FIG. 3). In the alternative, the main body 64a and the wall spacers 78 may be monolithically formed. The staple pusher tube 64 further defines diametrically opposed locking tabs 80 at its distal end which couple with the staple cartridge assembly 16 (see, e.g., FIGS. 3 and 11).

Figure 8:
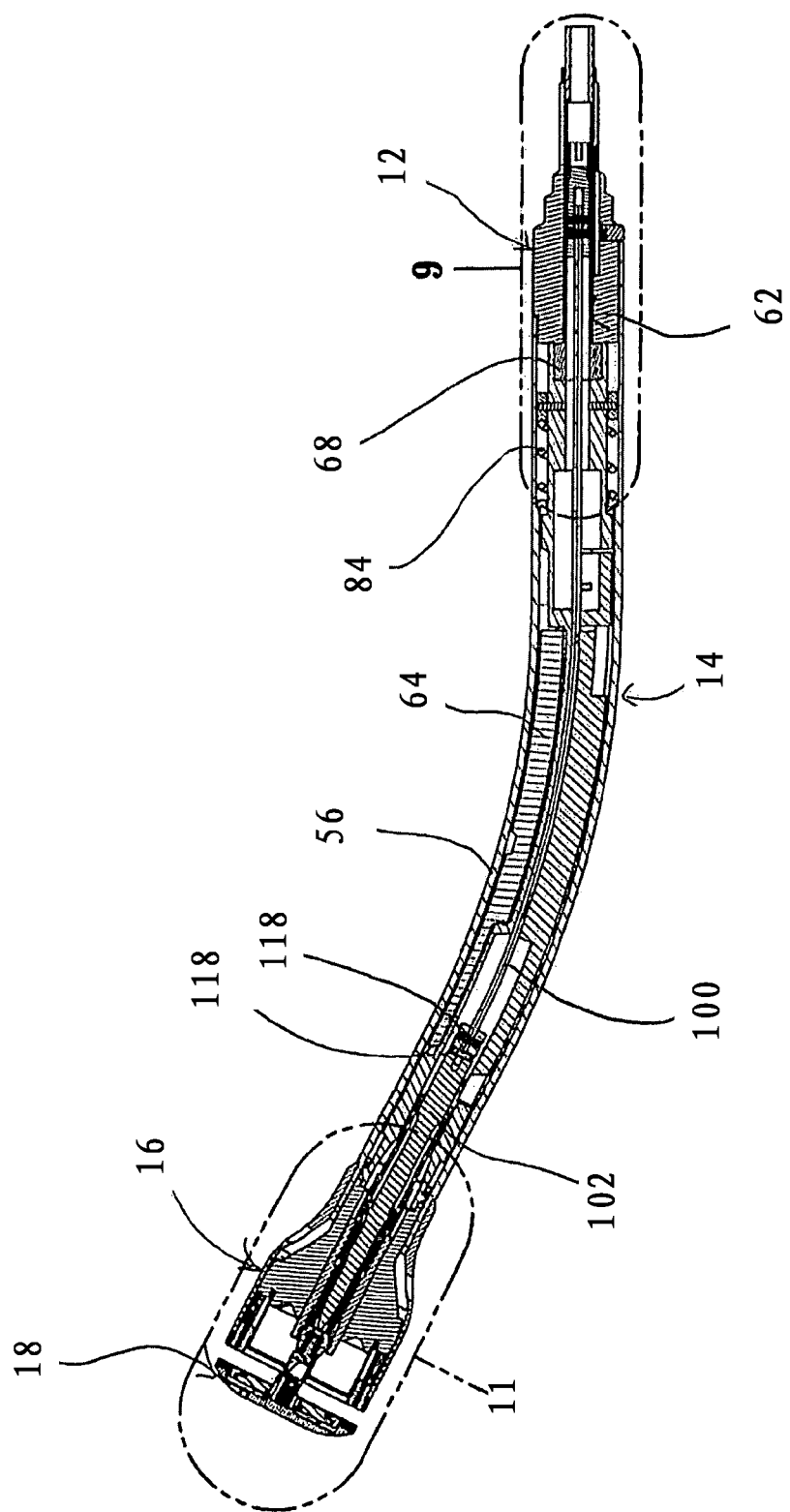
FIG. 8 is a side cross-sectional view of the surgical loading unit.

Referring to FIGS. 8-10, in conjunction with FIG. 3, the stapler pusher 60 is normally spring biased toward a proximal position. In one embodiment, the outer member 56 includes a washer 82 residing in an internal shelf 83 of the outer member 56 and a coil spring 84 which engages the washer 82 at the distal end of the coil spring 84. The staple pusher 60 includes a lock ring 86 which is secured to the proximal cylindrical segment 66 of the staple connector 62 (FIG. 3). The lock ring 86 includes lock pins 88 which extend through diametrically opposed openings 90 in the wall of the lock ring 86 and within aligned openings 92 in the wall of the staple connector 62 (FIG. 3). The lock pins 88 may be secured within the openings 90, 92 with the use of adhesives, cements or the like. The coil spring 84 engages the lock ring 86 to normally bias the lock ring 86 and the staple pusher 60 in a proximal direction.

Referring to FIGS. 8-11, an anvil approximator or drive 94 is at least partially disposed within the staple pusher 60 and the outer member 56. The anvil approximator 94 includes, from proximal to distal, an anvil sleeve 96, a connector 98 connected to the sleeve 96 and extending distally therefrom, a pair of elongate anvil bands 100 and an anvil retainer 102 coupled to the anvil bands 100. (see also FIG. 3) The anvil sleeve 96 includes structure which operatively engages at least one actuator within the handle assembly 1000. As depicted in FIG. 10, the structure may include a longitudinal opening 104 through which an anvil actuator of the handle assembly 1000 extends. The anvil sleeve 96 may define an internal shelf 105 or other coupling structure which engages with the anvil actuator of the handle assembly 1000. Other coupling mechanisms for coupling with the anvil actuator of the handle assembly 1000 are also envisioned.

Figure 12:
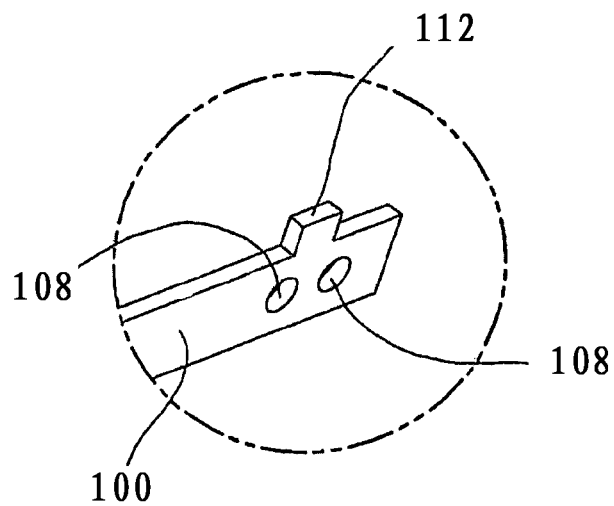
FIG. 12 is an isolated view of the area of detail identified in FIG. 3 illustrating the locking tabs of the anvil bands.

The connector 98 defines first and second legs 98a, 98b with pairs of opposed openings 106 extending through the walls of the legs 98a, 98b. (FIG. 3) The proximal ends of the anvil bands 100 are received within the legs 98a, 98b of the connector 98 and also define pairs of openings 108 which are in general alignment with the openings 106 of the connector 98. (See FIGS. 3 and 12). A pair of pins 110 extends through the openings 106, 108 to couple the connector 98 with the anvil bands 100. At least one, e.g., both, of the anvil bands 100 include locking tabs 112 adjacent the proximal ends of the anvil bands 100. (FIG. 12) The locking tabs 112 define anvil lock surfaces which are engaged by the lock tab 52 of the lock member 24 within the handle mount 12 to releasably secure the anvil approximator 94 in a first position which corresponds to a closed condition of the anvil assembly 18 relative to the staple cartridge assembly 16 (FIG. 10). Upon movement of the lock member 24 to the release position, the lock tab 52 of the lock member 24 releases the locking tabs 112 of the anvil bands 100 to permit longitudinal movement of the anvil approximator 94 to a second position corresponding to an open condition of the anvil assembly 18.

With reference again to FIGS. 3 and 8, the anvil retainer 102 includes a pair of retainer legs 114a, 114b with pairs of openings 116 extending through the retainer legs 114a, 114b. The distal ends of the anvil bands 100 are received within the retainer legs 114a, 114b and secured to the anvil retainer 102 via pins 118 which extend through the openings 116 in the legs 114a, 114b and the corresponding openings 120 defined within the anvil bands 100.

Figure 13:
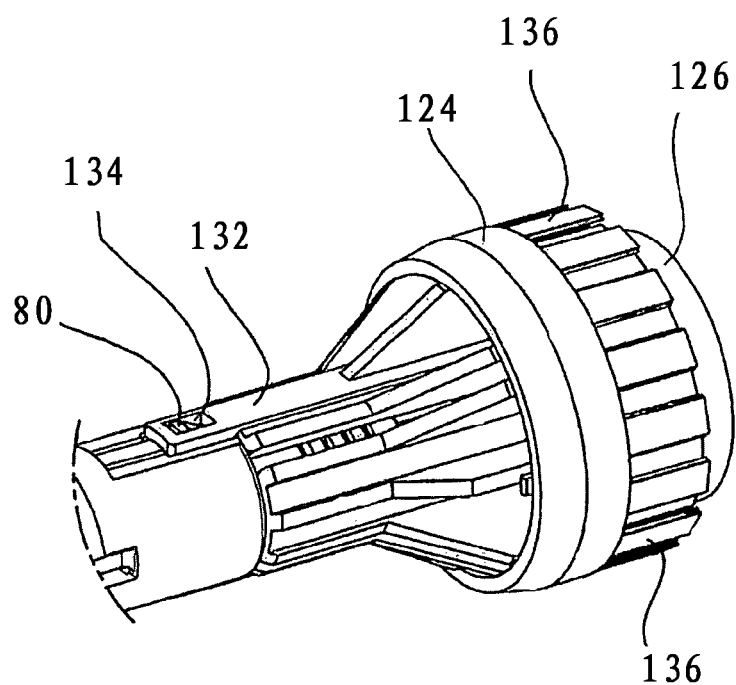
FIG. 13 is a perspective view of the staple cartridge assembly.

With reference now to FIGS. 11 and 13, in conjunction with FIG. 3, the staple cartridge assembly 16 will be discussed. The staple cartridge assembly 16 includes an outer shell 122, an annular staple pusher ring 124, a cylindrical knife 126 and a staple guide 128. In FIG. 13, the outer shell 122 is removed for illustrative purposes. The outer shell 122 is mounted to the outer member 56 through cooperative engagement of shell locking detents 130 of the outer shell 122 with the rectangular shaped windows 58 of the outer member 56. (FIG. 3) The outer member 56 may define a reduced diameter which receives the shell 122 to maintain a substantial constant diameter through most of the length of the elongated segment 14. The pusher ring 124 includes a pair of locking legs 132 at its proximal end. The locking legs 132 include openings 134 which receive the locking tabs 80 of the staple pusher tube 64 to couple the staple pusher 60 with the staple pusher ring 124. Thus, movement of the staple pusher 60 causes corresponding movement of the staple pusher ring 124. The staple pusher ring 124 defines a plurality of pusher elements 136 arranged in a circular or annular array. The cylindrical knife 126 is at least partially received within an annular groove or channel 138 within the interior of the staple pusher ring 124, and may be secured within the pusher ring 124 via the use of adhesives or other means (FIG. 11). The staple guide 128 includes a plurality of staples 140 also arranged in an annular array. The staples 140 are ejected upon advancement of the staple pusher 60, the staple pusher ring 124 and the pusher elements 136.

The anvil assembly 18 includes an anvil shaft 142 and an anvil head 144 connected to the anvil shaft 142. (FIGS. 3 and 11) The anvil head 144 includes an annular anvil surface 146 which cooperates with the staples 140 to crimp the staples 140 during firing of the loading unit 10. The anvil shaft 142 is couplable to the anvil retainer 102. In one embodiment, the anvil shaft 142 includes one or more internal locking shelves 148 which cooperate with the outer locking ledge 150 on the anvil retainer 102 to releasably secure the anvil shaft 142 to the anvil retainer 102. The anvil shaft 142 may have sufficient resiliency or incorporate one or more deflectable components whereby the shaft 142 expands in diameter to receive the anvil retainer 102, and then returns towards its original diameter with the internal locking shelves 148 engaging the outer ledge 150 on the anvil retainer 102. Removal of the anvil assembly 18 relative to the anvil retainer 102 may be effected by pulling on either or both the anvil assembly 18 and the anvil retainer 102 to cause the anvil shaft 142 to expand in diameter such that the locking shelves 148 clear the outer locking ledge 150 of the anvil retainer 102. The anvil head 144 may articulate about pivot pin 152.

Figure 14:
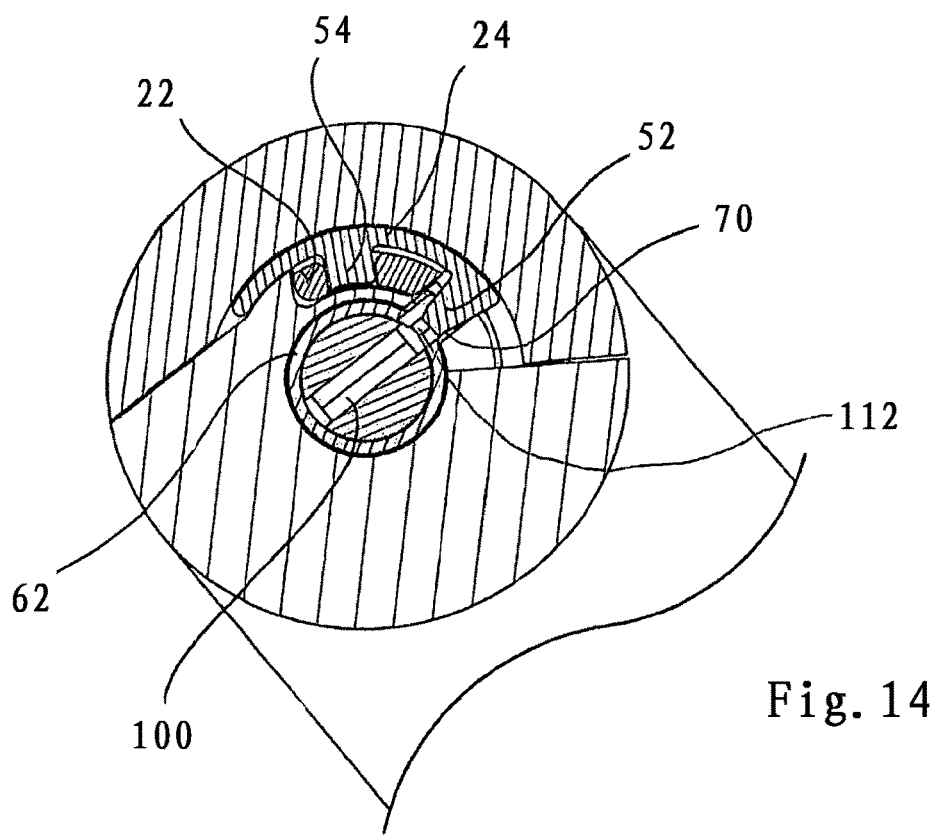
FIG. 14 is a cross-sectional view taken along the lines 14-14 of FIG. 6 illustrating the lock member in the lock position in secured engagement with the staple pusher and the anvil approximator.

The use and operation of the surgical loading unit 10 and the handle assembly 1000 will now be discussed. As best depicted in FIG. 14, prior to mounting of the loading unit 10 to the handle assembly 1000, the lock member 24 is in the lock position in secured engagement with the staple pusher 60 and the anvil approximator 94. (see also FIG. 10) Specifically, the lock tab 52 of the lock member 24 is received within the lock slot 72 of the raised spline 70 of the staple connector 62, and also engages the locking tabs 112 of the anvil bands 100 of the anvil approximator 64. As discussed, the lock member 24 is normally biased to the lock position by the coil spring 50 which is engagement with the guide member 24 and normally biases the guide member 24 to its retracted position.

With reference now to FIGS. 15A-15C, the loading unit 10 is advanced toward the handle frame 1002 of the handle assembly 1000 with the outer tabs 32 and the alignment tab 34 of the loading unit 10 in general alignment with respective grooves 1004, 1006 (shown in phantom) of the handle frame 1002. The handle mount 12 is inserted within the handle frame 1002 of the handle assembly 1000. The loading unit 10 may be secured to the handle frame 1002 through rotation of the loading unit 10 to establish a bayonet coupling with the outer tabs 32 of the loading unit 10 and cooperating grooves 1004, 1006 of the handle assembly 1000. Other mechanisms for securing the loading unit 10 and the handle assembly 1000 are also envisioned including, e.g., a snap-lock relationship.

Figure 16:
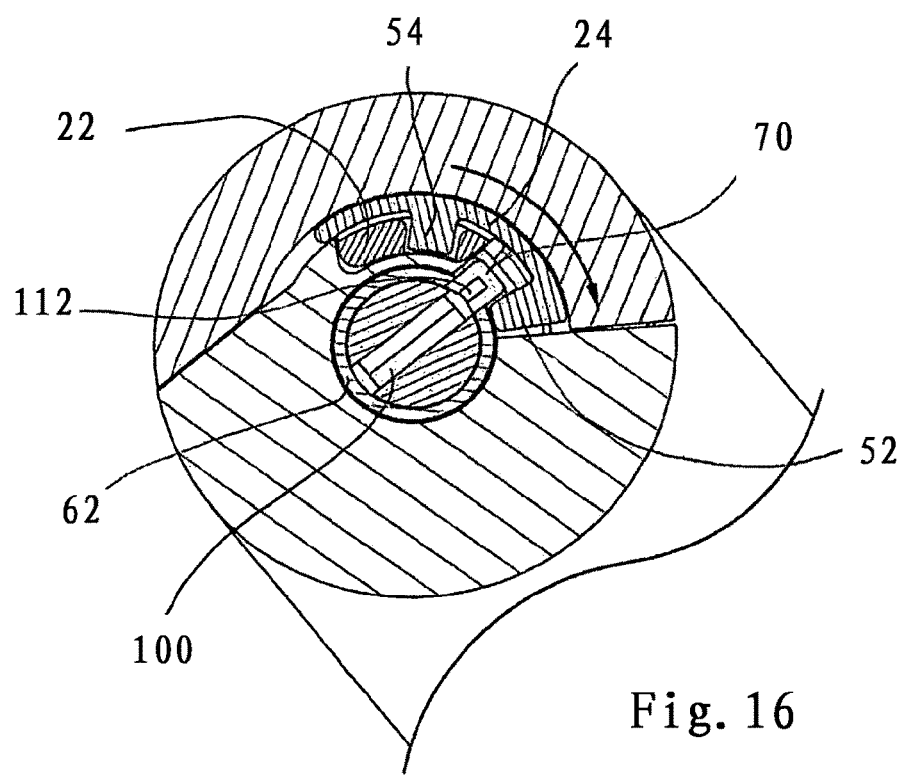
FIG. 16 is a cross-sectional view taken along the lines 16-16 of FIG. 7 illustrating the lock member in the release position releasing the staple pusher and the anvil approximator.
Figure 17:
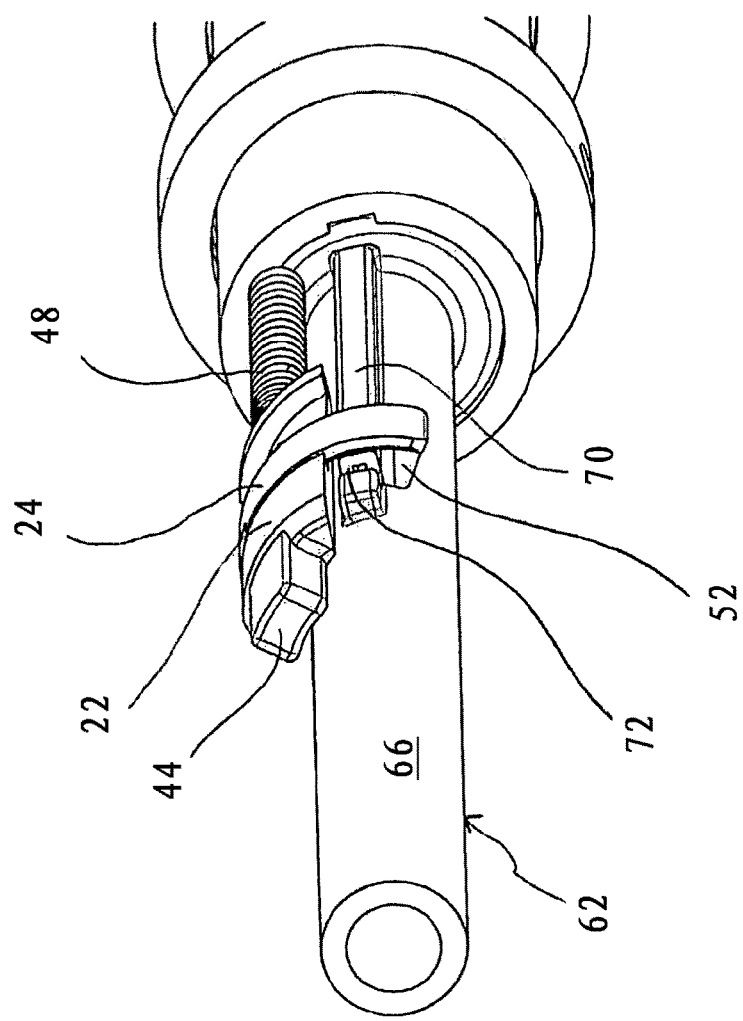
FIG. 17 is a perspective view of a portion of the handle mount illustrating the lock member in the release position.

Upon mounting of the handle mount 12 within the surgical handle assembly 1000, the proximal guide tab 44 of the guide member 22 is engaged by corresponding structure within the handle assembly 1000 and is driven against the bias of the coil spring 50 in the direction of directional arrow "t" (FIGS. 7 and 15C). The corresponding structure may be an internal shelf, detent or similar structure identified schematically (in phantom) as reference numeral 1008, within the interior of the handle frame 1002. Movement of the guide member 22 causes the lock member 24 to rotate through a predetermined arc of rotation from the lock position of FIG. 14 to the released position of FIGS. 16 and 17 such that the lock tab 52 of the lock member 24 releases the lock slot 72 of the staple connector 62 and also releases the locking tabs 112 of the anvil bands 100 of the anvil approximator 94. In this position of the lock member 24, the staple pusher 60 and the anvil approximator 94 are free for longitudinal movement.

In addition, during mounting of the handle mount 12, at least one, e.g. first and second actuators, within the handle frame 1002 of the handle assembly 1000 couple with the anvil approximator 94 and the staple pusher 60. Any mechanisms for coupling the actuators of the handle assembly 1000 with the anvil approximator 94 and staple pusher 60 are envisioned, including, e.g., a bayonet coupling, interference fit or any other keyed or non-keyed coupling mechanisms. For example, with reference to FIGS. 18 and 19, the first or anvil actuator of the handle assembly 1000, identified schematically (in phantom) as reference numeral 1010, may be coupled to the anvil sleeve 96 through insertion of the distal end of the first actuator 1010 through the longitudinal opening 104 of the anvil sleeve 96. (FIG. 10). The first actuator 1010 may have a spring-biased detent which flexes inwardly to be passed through the longitudinal opening 104, and then returns under the influence of its normal spring bias to engage the internal shelf 105 of the anvil sleeve 96 to couple the components. The second or staple actuator of the handle assembly 1000, identified schematically (in phantom) as reference numeral 1012 in FIG. 20, may abut or engage the proximal end of the staple connector 62. Other arrangements are also envisioned.

Figure 18:
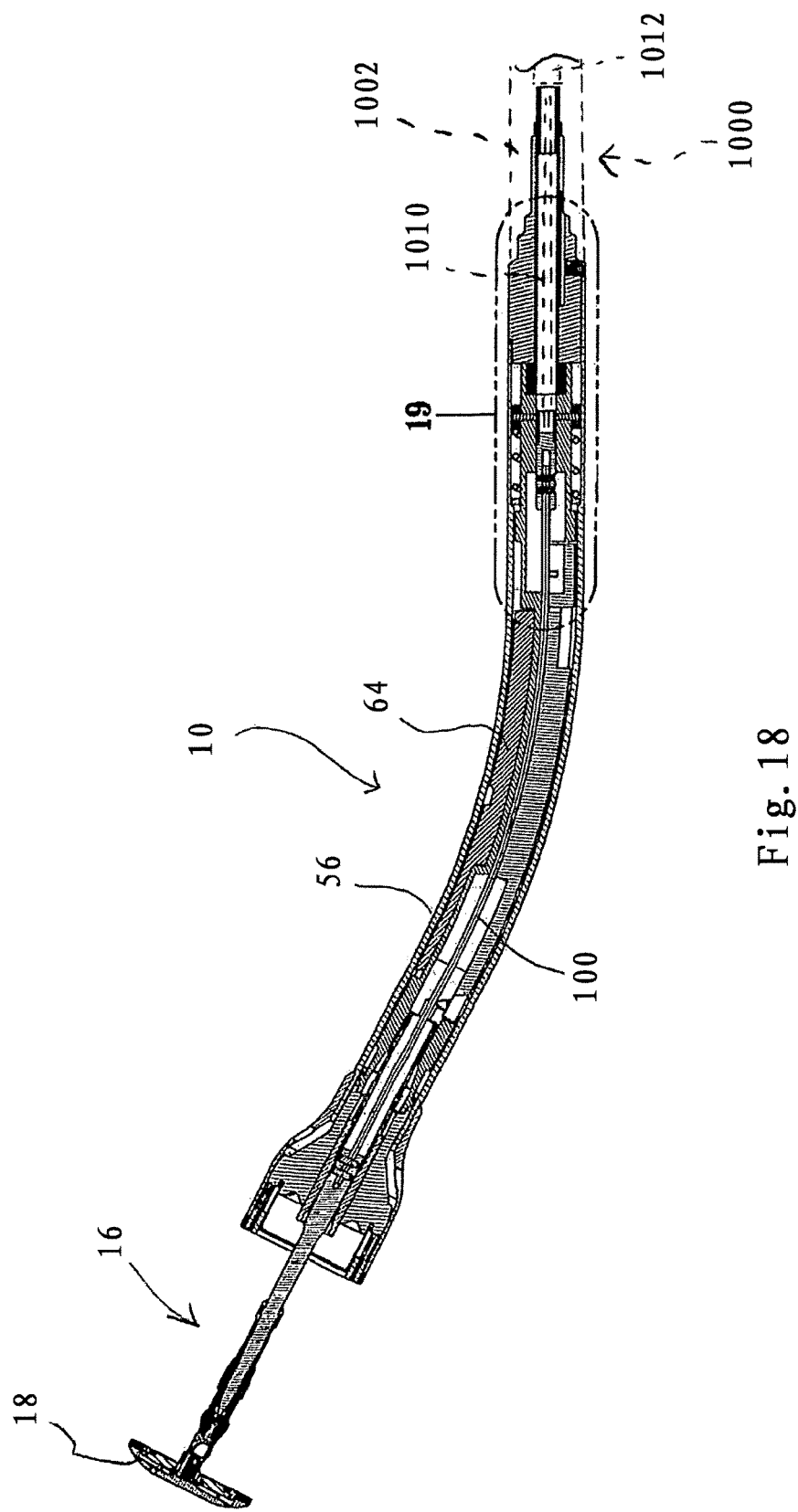
FIG. 18 is a side cross-sectional view of the loading unit with a segment of the surgical handle assembly in phantom, illustrating the anvil assembly in an open condition upon advancement of the anvil approximator.
Figure 19:
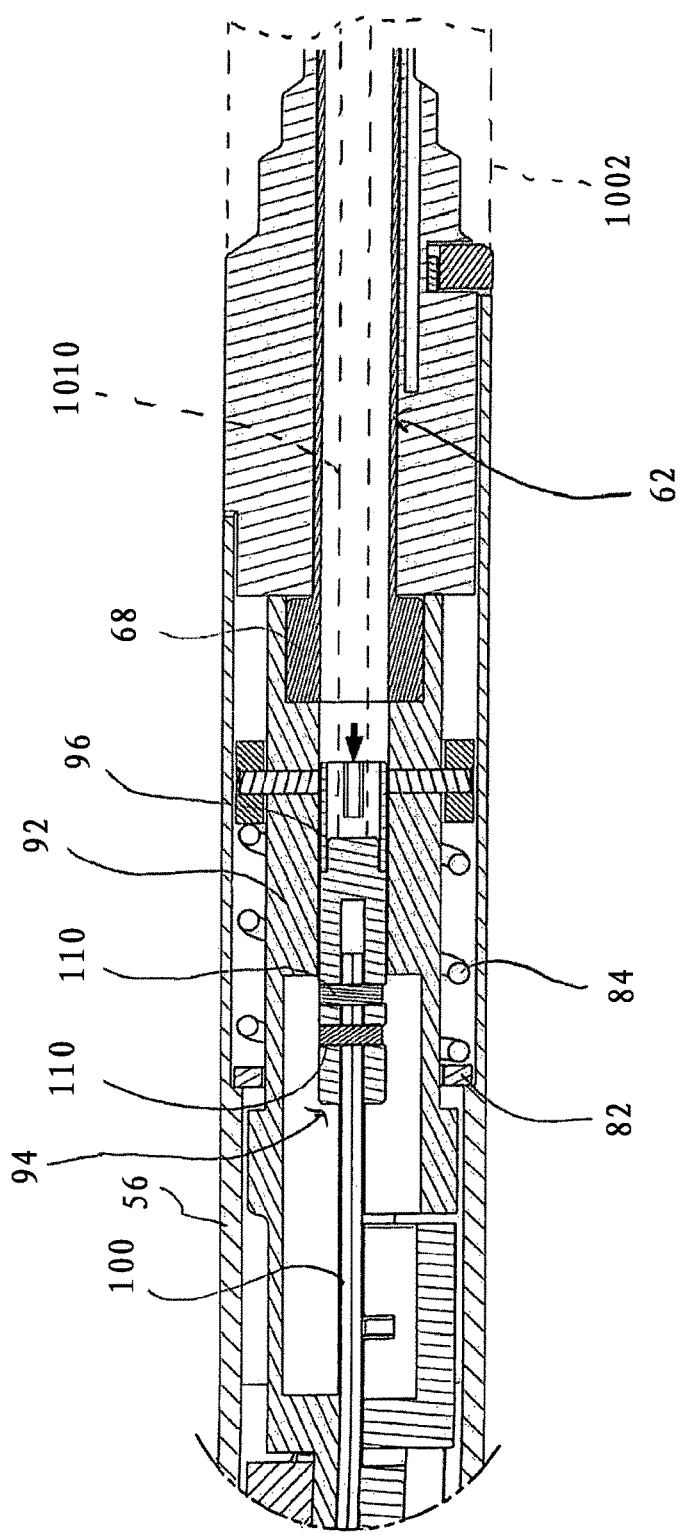
FIG. 19 is an isolated view of the area of detail of FIG. 18.
Figure 20:
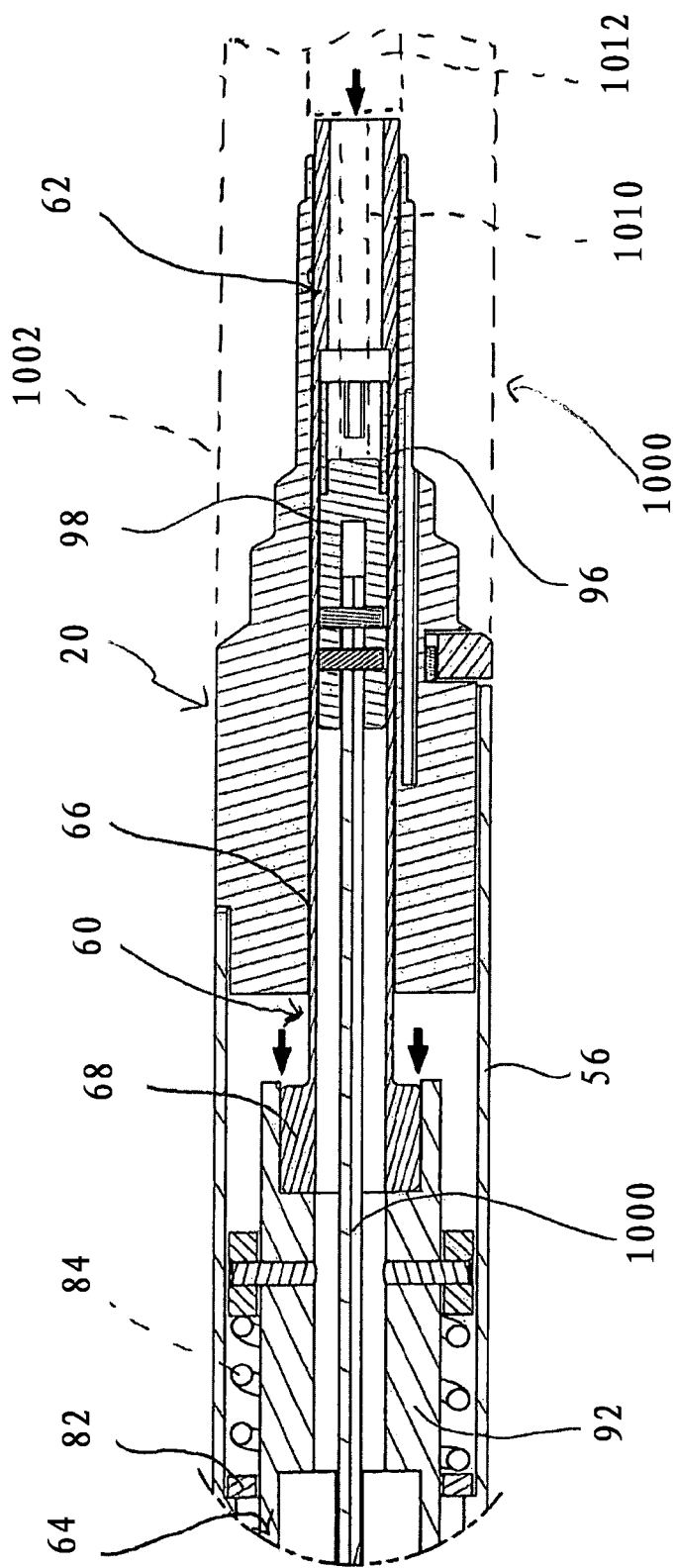
FIG. 20 is a side cross-sectional view of the handle mount with a segment of the surgical handle assembly in phantom, illustrating the staple pusher advanced to fire the staples from the staple cartridge assembly.

The procedure may be continued by advancing the anvil actuator 1010 of the handle assembly 1000 via manual member 1014 (FIG. 2) connected to the anvil actuator 1010 (by conventional means) to move the anvil approximator 94 (including the anvil sleeve 96 and the anvil bands 100) in the distal direction from its first position to its second position to cause distal displacement of the anvil assembly 18 to its open condition relative to the staple cartridge assembly 16 (FIGS. 18 and 19). Prior or subsequent to advancement of the anvil approximator 94, the anvil retainer 102 may be mounted to the anvil shaft 142 of the anvil assembly 18 in the manner discussed hereinabove. The anvil assembly 18 may be positioned relative to a tubular organ or tissue and the anvil approximator 94 may be returned to its first position, as depicted in FIG. 20, by movement of the anvil actuator 1010 via manual member 1014 of the handle assembly 1000 in, e.g., a proximal direction, to position the anvil assembly 18 in its closed condition (FIG. 2) relative to the staple cartridge assembly 16. The staple cartridge assembly 16 is positioned relative to the tissue. Thereafter, the staple actuator 1012 of the handle assembly 1000 is actuated via manual member 1016 of the handle assembly 1000 (FIG. 2), which is connected to the staple actuator 1012 by conventional means, to advance the staple actuator 1012 and the staple connector 62 (and the staple pusher 60) as depicted in FIG. 20. Advancement of the staple connector 62 causes corresponding advancement of the staple pusher ring 124 and the cylindrical knife 126 of the staple cartridge assembly 16 to expel the staples 140 which are crimped by the anvil surface 146 of the anvil head 144 thereby joining the tissue or tubular organs and creating an opening therebetween with the cylindrical knife 146.

Subsequent to use of the loading unit 10, the loading unit 10 may be released from the handle assembly 1000 and disposed, or reloaded and sterilized for subsequent use. Alternatively, a second loading unit 10 can be mounted to the handle assembly 1000 to perform additional stapling or fastening functions and/or other procedures.

It will be understood that various modifications may be made to the embodiments disclosed herein. For example, the above described lockout mechanism may be incorporated into a variety of surgical instruments which include loading units and is not solely limited to use on staplers systems adapted to perform an end-to-end or circular anastomosis of tissue. For example, the loading unit may be adapted to fire clips or any other fastener dimensioned to attach tissue, including linear attachment of tissue. Therefore, the above description should not be construed as limiting, but merely as exemplifications of various embodiments. Those skilled in the art will envision other modifications within the scope and spirit of the claims appended hereto.

What is claimed is:

1. A surgical loading unit for use with a surgical handle assembly, which comprises:
   a handle mount dimensioned for mounting to the handle assembly;
   an outer member extending from the handle mount and defining a longitudinal axis and having proximal and distal ends;
   a staple cartridge assembly mounted to the distal end of the outer member, the staple cartridge assembly including a plurality staples;
   an anvil assembly couplable relative to the staple cartridge assembly;
   a staple pusher at least partially disposed within the outer member and operatively coupled to the staple cartridge assembly, the staple pusher adapted for longitudinal movement to eject the staples;
   an anvil approximator at least partially disposed within the outer member and operatively coupled to the anvil assembly, the anvil approximator movable independently of the staple pusher between first and second positions corresponding to closed and open conditions of the anvil assembly relative to the staple cartridge assembly; and
   a lock member mounted to the handle mount, the lock member movable from a lock position in secured engagement with both the staple pusher and the anvil approximator to a release position to simultaneously release the staple pusher and the anvil approximator upon mounting of the handle mount relative to the surgical handle assembly.

2. The surgical loading unit according to claim 1 wherein the lock member is adapted for rotational movement about the longitudinal axis to move from the lock position to the release position.

3. The surgical loading unit according to claim 2 including a guide member having a guide channel arranged at an angle relative to the longitudinal axis, the lock member at least partially received within the guide channel of the guide member and adapted to traverse the channel during movement of the lock member from the lock position to the release position.

4. The surgical loading unit according to claim 3 wherein the lock member includes a lock tab and a channel tab, the lock tab operatively engagable with the staple pusher and the anvil approximator when the lock member is in the lock position, the channel tab received within the guide channel and adapted to traverse the channel.

5. The surgical loading unit according to claim 3 wherein the guide member is adapted to move relative to the handle mount between a retracted position corresponding to the lock position of the lock member and an advanced position corresponding to the release position of the lock member.

6. The surgical loading unit according to claim 5 wherein the guide member is normally biased toward the retracted position.

7. The surgical loading unit according to claim 6 including a spring operatively engagable with the handle mount and the guide member, and dimensioned to normally bias the guide member to the retracted position.

8. The surgical loading unit according to claim 5 wherein the guide member is dimensioned to engage the handle assembly during mounting of the handle mount relative to the handle assembly causing movement of the guide member to the advanced position thereof.

9. The surgical loading unit according to claim 2 wherein the staple pusher includes a staple connector at least partially disposed within the handle mount, the staple connector having a staple lock surface, the staple lock surface engaged by the lock member when in the lock position thereof and released from the lock member when in the release position thereof.

10. The surgical loading unit according to claim 9 wherein the staple pusher is normally biased toward a proximal position thereof.

11. The surgical loading unit according to claim 9 wherein the anvil approximator includes an anvil band at least partially disposed within the handle mount, the anvil band having an anvil lock surface, the anvil lock surface engaged by the lock member when in the lock position thereof and released from the lock member when in the release position thereof.

12. The surgical loading unit according to claim 1 wherein the staple cartridge includes an annular array of staples and the anvil assembly includes an annular anvil head cooperable with the annular array of staples to perform a circular or an end-to-end anastomosis.

13. A surgical system for performing an anastomosis, which comprises:
   a handle assembly including:
      a frame;
      a staple actuator and an anvil actuator at least partially disposed within the frame; and
      at least one manual member for actuating at least one of the staple actuator and the anvil actuator;
   a loading unit including:
      a handle mount dimensioned for mounting to the frame of the handle assembly;
      an outer member extending from the handle mount and defining a longitudinal axis and having proximal and distal ends;
      a staple cartridge assembly mounted to the distal end of the outer member, the staple cartridge assembly including a plurality staples arranged in a circular array;
      an anvil assembly couplable relative to the staple cartridge assembly, the anvil assembly including an anvil shaft and an anvil head;
      a staple pusher at least partially disposed within the outer member and operatively coupled to the staple cartridge assembly, the staple pusher adapted for longitudinal movement to eject the staples, the staple pusher couplable to the staple actuator of the handle assembly upon mounting of the handle mount to the frame whereby movement of the at least one manual member causes corresponding movement of the staple pusher; and
      an anvil approximator at least partially disposed within the outer member and operatively coupled to the anvil assembly, the anvil approximator movable independently of the staple pusher between first and second positions corresponding to closed and open conditions of the anvil assembly relative to the staple cartridge, the anvil approximator couplable to the anvil actuator of the handle assembly upon mounting of the handle mount to the frame whereby movement of the at least one manual member causes corresponding movement of the anvil approximator between the first and second positions; and
      a lockout mechanism mounted to the handle mount, the lockout mechanism including a lock member and a guide member, the guide member engageable with the frame of the handle assembly upon mounting of the handle mount to the frame of the handle assembly to cause the lock member to rotate about the longitudinal axis from a lock position where the lock member is in secured engagement with both the staple pusher and the anvil approximator, to a release position where the lock member simultaneously releases the staple pusher and the anvil approximator.

14. The surgical system according to claim 13 wherein the guide member is adapted to move relative to the handle mount between a retracted position corresponding to the lock position of the lock member and an advanced position corresponding to the release position of the lock member.

15. The surgical system according to claim 14 wherein the lock member includes a channel tab and a locking tab, the locking tab engageable with the staple pusher and the anvil approximator when in the lock position of the lock member, the channel tab received within a guide channel defined within the guide member, the channel tab traversing the guide channel upon movement of the guide member between the retracted position and the advanced position.

16. The surgical system according to claim 15 wherein the guide member is normally biased toward the retracted position thereof.

17. The surgical system according to claim 14 wherein the staple pusher is normally biased toward a proximal position thereof.

* * * * *